United States Patent [19]

Diamond

[11] 4,422,849
[45] Dec. 27, 1983

[54] DENTAL INSTRUMENT AND METHOD FOR POSITIONING A LINGUAL ORTHODONTIC BRACKET

[76] Inventor: Michael K. Diamond, 86 Milburn La., Roslyn, N.Y. 11577

[21] Appl. No.: 322,193

[22] Filed: Nov. 17, 1981

[51] Int. Cl.³ .............................................. A61C 7/00
[52] U.S. Cl. .................................................... 433/3
[58] Field of Search ......................... 33/334, 389, 390

[56] References Cited

U.S. PATENT DOCUMENTS 3,871,098  3/1975  Dean ....................................... 433/3

OTHER PUBLICATIONS

Dental Abstracts Mar. 1966, vol. 11 #3 p. 149, "Position Finder for Prevailing Prepartions".

Primary Examiner—Robert Peshock

[57] ABSTRACT

A dental instrument and method for positioning a lingual orthodontic bracket is disclosed. The instrument comprises a housing on which is positioned an arm that includes means for releasably holding the orthodontic bracket. Level indicating means are used for displaying the extend of inclination of the arm with respect to a predetermined plane.

30 Claims, 12 Drawing Figures

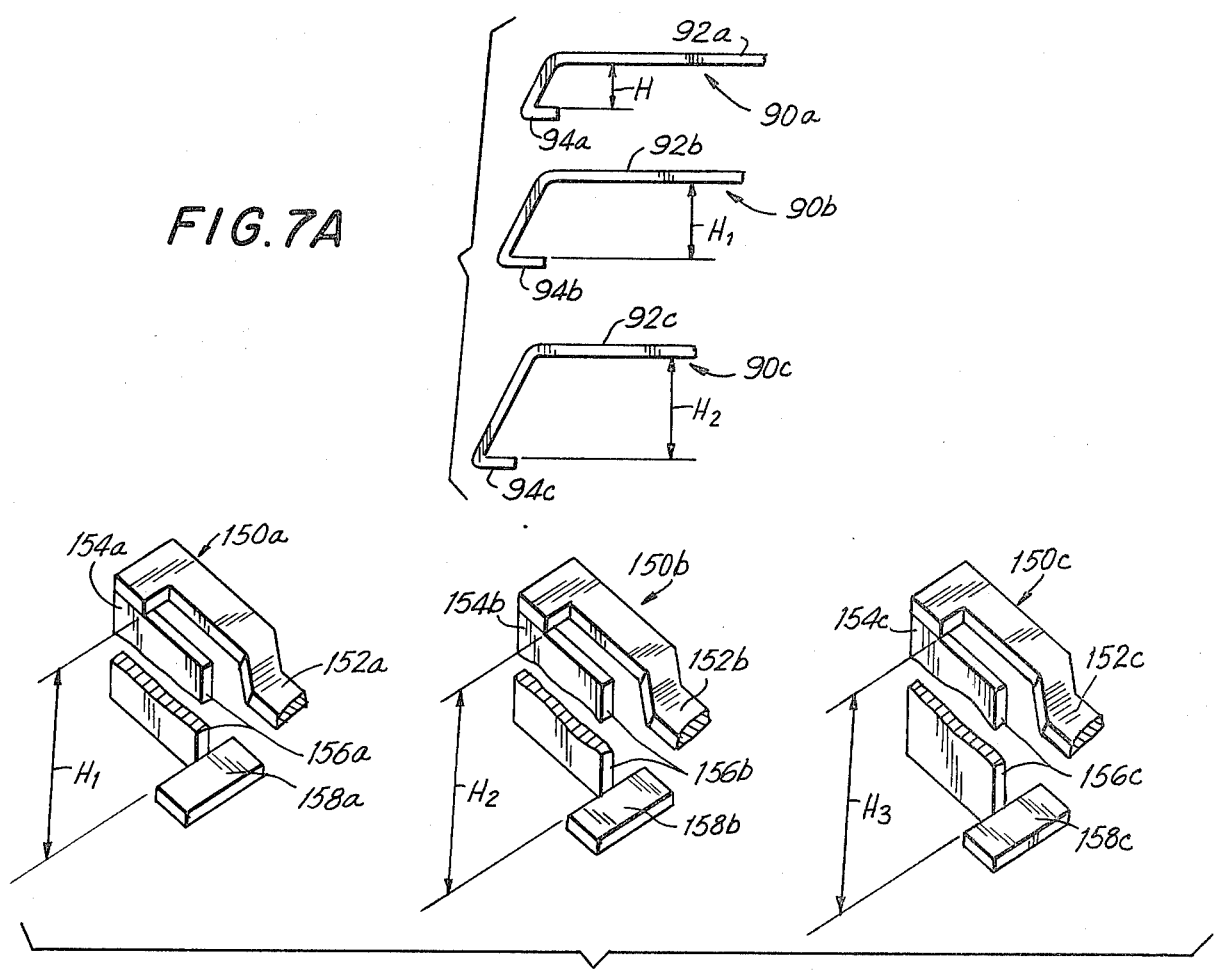
FIG.7A
FIG.7B
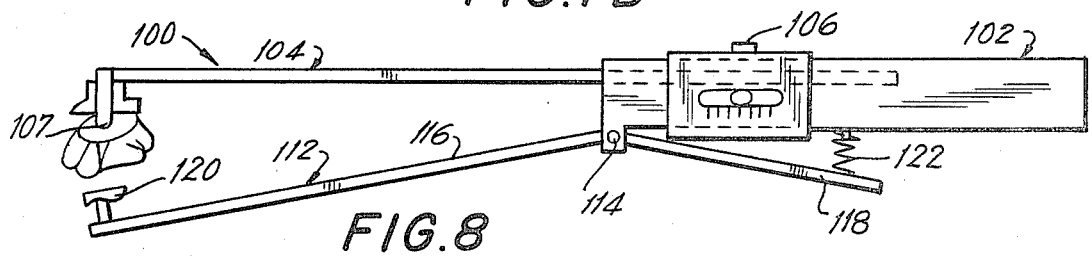
FIG.8
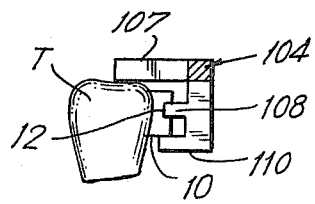
FIG.9A
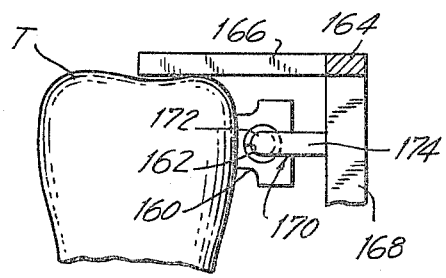
FIG.9B

DENTAL INSTRUMENT AND METHOD FOR POSITIONING A LINGUAL ORTHODONTIC BRACKET

The present invention relates generally to dental instruments and more particularly to an improved instrument and method for positioning a lingual, orthodontic bracket.

The method most commonly used today for orthodontic treatment involves the correction of malocclusions by attaching metal or plastic brackets to the facial surfaces of teeth. A U-shaped wire is then fitted into these brackets and the position of the misaligned teeth is corrected by sliding the teeth along the wire, using either a pushing or a pulling force. More specifically, and in this prior art method, individual brackets or metal bands with brackets attached to them are secured such as by the use of cement to the facial surface of each tooth. The brackets each have a horizontal and/or vertical slot that is perpendicular and/or parallel, respectively, to the longitudinal axis of the tooth with the slot, when it is horizontal, being at a set distance from the incisal edge or cusp tip of the tooth. An arch wire is positioned in the slots and is secured to the brackets by means of ligatures or pins.

The primary disadvantage of this conventional method is that the brackets and the wires are visible when the mouth is opened because the appliance is attached to the outer surface of the teeth. It will be evident that the profession of many people, particularly adults, precludes the possibility of wearing orthodontic braces of this type. Such group of people would include actors, actresses, business executives, sales people, athletes, etc.

Another prior art form of treating malocclusions utilized metal bands with brackets that were cemented to the molars. A lingually located, heavy arch wire was then attached to the bands and individual ligatures were used to connect the teeth to the arch wire. The ligatures were then periodically tightened. However, because this method of treating malocclusions from the lingual side did not attach each tooth to the arch wire by means of a bracket secured to the tooth, the movements of the teeth were unpredictable and inaccurate. Generally speaking results achieved by this second method were not satisfactory.

The present invention, by way of contrast, utilizes individual brackets, each having a horizontal or vertical slot or both. The brackets are individually cemented to the lingual surface of its respective tooth. If desired or required, orthodontic bands with lingual tubes and buccal or facial attachments are cemented on the molar teeth.

In order to practice the method comprising the present invention, an arch wire is passed into the lingual tubes on the brackets which are mounted on the molars and is engaged in the horizontal or vertical slots of the remaining brackets. The arc wire is held in place by ligatures. If more than one molar is banded or if a bracket will not adhere to the lingual side of the tooth, a bracket could be placed on the facial side of the tooth and a wire used to connect the bracket on the tooth to the bracket on a molar. Alternatively, two molars could be secured to each other in the same manner. Normally, the molars are utilized as an anchorage and serve to apply a resistance force.

In the event of a deep bite where closure of the mouth causes the teeth to hit the brackets, for example the lower teeth hitting the upper brackets, two different courses of treatment could be used. First of all, only the lower teeth could be treated until the condition is corrected. Alternatively, a removable plastic wafer that covers the occlusal surfaces of the upper or lower teeth could be utilized to prevent the brackets from being traumitized.

The method comprising the present invention contemplates moving the teeth by periodically changing the size of the arch wire or using the same size wire but of a different resiliency or a combination of both. The brackets are usually placed on or close to the vertical center line of the teeth. The dimension or distance of the bracket from the incisal edge or cusp tip varies from tooth to tooth. For example, the brackets placed on the four lower incisors could be at the same level but the bracket placed on the lower canines would be 0.5 mm further from the edge of the tooth. Normally the vertical center line is determined either by eye, by calipers or by use of a divider because the precise location is not too critical. However, the height or dimension of the edge of the bracket from the incisor ledge or cusp tip of the tooth is critical because, ideally, the teeth should be in a common plane.

Prior to the use of the method and apparatus comprising the present invention, accurate placement of lingual brackets with respect to the incisal edge or cusp tip of the teeth was very difficult if not impossible to do directly on the patient's teeth. It should be kept in mind that time is an additional factor which must be considered. Because the adhesive utilized in cementing brackets used in an orthodontic practice sets relatively fast, the brackets must not only be accurately placed but must also be placed rather quickly.

To the best of my knowledge no instrument presently exists that accurately positions a lingual bracket in the mouth of the patient on or parallel to the vertical center line of a tooth at a predetermined distance from the incisal edge or cusp tip of the tooth.

The present invention provides an instrument for accurately positioning a lingual orthodontic bracket, for example, on a tooth in the mouth of a patient and includes a housing from which an arm extends. Retaining means are formed integrally with the arm for the purpose of releasably holding an orthodontic bracket utilizing either a vertical or a horizontal slot therein. Further, the retaining means in one embodiment of this invention may be releasably applied to a lingual tube formed on an orthodontic bracket.

When a portion of the arm of the instrument comprising this invention rests on the top surface of the tooth, a level indicating device will display the extent of inclination of the arm with respect to a predetermined plane, such as the horizontal plane. The instrument comprising the present invention provides means for adjusting the position of the arm in a plane that is either substantially parallel, perpendicular or oblique to the predetermined plane. Advantageously, the instrument comprising this invention further includes an adjustably mounted plate that is located in opposition to that end of the arm which is remote from the housing in order to engage the facial surface of the tooth when the bracket is positioned on the lingual surface of the tooth.

In one embodiment of the present invention the means for displaying the extent of inclination of the arm with respect to the predetermined plane is in the form of a bubble level mounted in the housing and on which indicia are provided adjacent the bubble level. In order to permit usage of the present invention with both upper and lower teeth, the level indicating means should be on both upper and lower surfaces of the housing.

Accordingly, it is an object of the present invention to provide an improved orthodontic instrument.

Another important object of the present invention is to provide an improved instrument as described above, for positioning an orthodontic bracket on a tooth.

Still another object of the present invention is to provide an improved instrument, as described above, for positioning a lingual orthodontic bracket on a tooth.

An additional object of the present invention is to provide an improved dental instrument, as described above for positioning a lingual orthodontic bracket on a tooth in the mouth of a patient.

A further object of the present invention is to provide an improved orthodontic instrument, as described above, including means for displaying the extent of inclination of a portion of the instrument with respect to the predetermined plane.

It is another object of the present invention to provide an improved orthodontic instrument, as described above, including means for releasably holding the orthodontic bracket prior to the placement thereof on the lingual surface of the tooth.

An additional object of the present invention, is to provide an improved orthodontic instrument, as described above, including means that can adjustably position a lingual orthodontic bracket either in a plane substantially parallel, perpendicular or oblique with respect to the longitudinal axis of the tooth.

Yet another object of the present invention is to provide an improved orthodontic instrument, as described above, that further includes an adjustable plate in spaced opposition to that portion of the instrument that releasably supports the orthodontic bracket with the plate being adapted to engage the facial surface of the tooth when the bracket is positioned on the lingual surface of the tooth.

A specific object of the present invention is to provide an improved orthodontic instrument, as described above, wherein the level indicating means comprises a bubble level on at least one surface of the instrument and preferably comprises two bubble levels on surfaces of the instrument that are 180° apart but parallel to each other so that the instrument may be used on both the upper and lower sets of teeth.

It is another object of the present invention to provide an improved orthodontic instrument, as described above, wherein there is included a plurality of means for releasably holding the orthodontic bracket, the plurality of means having a range of dimensions defining a set of means for holding the orthodontic bracket.

An important object of the present invention is to provide an improved orthodontic instrument, as described above, wherein the level indicating means for displaying the extent of inclination of a portion of the instrument with respect to an orthodontic bracket and a predetermined plane includes means responsive to rotation of the instrument about a plane that is substantially parallel to the vertical axis of the tooth.

Another important object of the present invention is to provide an improved orthodontic instrument, as described above, that is adapted to releasably support a lingual orthodontic bracket utilizing the horizontal slot thereof.

An additional object of the present invention is to provide an improved orthodontic instrument, as described above, that is adapted to support a lingual orthodontic bracket utilizing the vertical slot thereof.

Yet another object of the present invention is to provide an improved orthodontic instrument, as described above, that is adapted to releasably support a lingual bracket that includes a tube for receiving a lingual arch wire, the instrument including a pin that is arranged to be inserted into the lingually located tube on the bracket.

These and other objects, features and advantages of the invention will, in part, be pointed out with particularly, and will, in part, become obvious from the following more detailed description of the invention, taken in conjunction with the accompanying drawings, which forms an integral part thereof.

In the drawings, like reference characters designate like parts. In the drawings:

FIG. 7A is a schematic illustration of a portion of the instrument shown in FIG. 3 illustrating the applicability thereof as a set of instruments having a range of dimensions;

FIG. 7B is a schematic illustration of a portion of the instrument shown in FIG. 6B showing the applicability thereof as a set of instruments having a range of dimensions;

FIG. 8 is a schematic plan view illustrating an alternative embodiment of the improved orthodontic instrument comprising the invention;

FIG. 9A is a transverse elevational view, partially in section, taken along 9—9 of FIG. 8; and FIG. 9B is a fragmentary elevational view, partially in section, illustrating an alternative embodiment of the structure shown in FIG. 9A.

Figure 1:
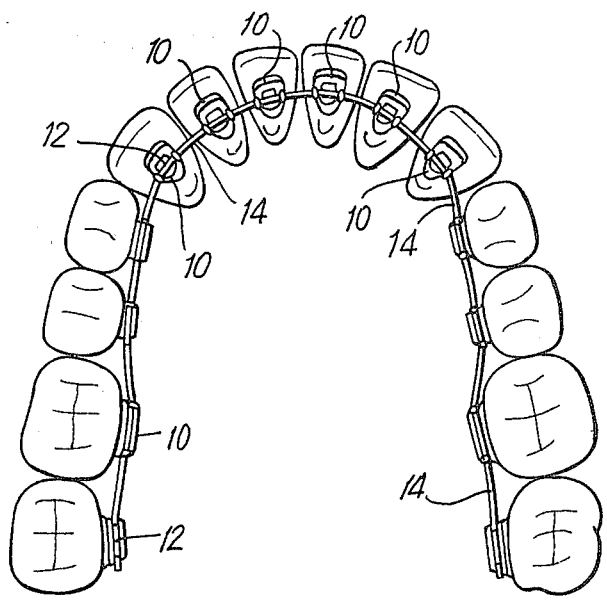
FIG. 1 is a plan view of the mandibular arch illustrating a plurality of lingual, orthodontic brackets adhesively secured to the teeth together with an arch wire held in place by means of ligatures.
Figure 2:
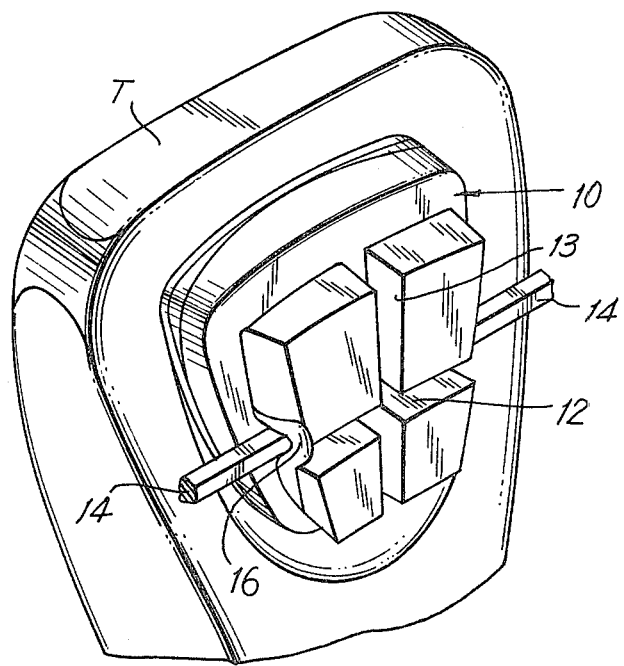
FIG. 2 is an enlarged perspective view of a typical orthodontic bracket used in FIG. 1.

Referring first to FIGS. 1 and 2, there is shown therein a plurality of orthodontic brackets each designated by the reference character 10 and which are each adhesively secured to the lingual surface of the mandibular arch but which, per se, do not form part of the present invention. While there are many different types of brackets 10, each of which has its own special function depending upon the tooth T to which it is applied, the single feature common to all of the brackets 10 which is of importance to the present invention is the transverse and/or vertical slots 12, 13 respectively, shown best in FIG. 2. In a manner well known in the art, an arch wire 14 is positioned in the slots 12, for example, and is resiliently and removably secured to the brackets 10 by means of elastic liguatures 16.

Figure 3:
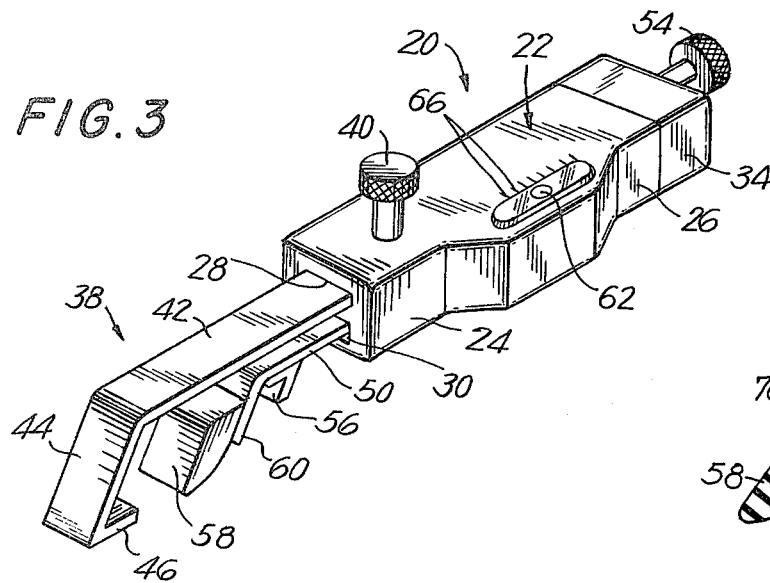
FIG. 3 is a schematic, perspective view illustrating one embodiment of the improved orthodontic instrument comprising the present invention.
Figure 4:
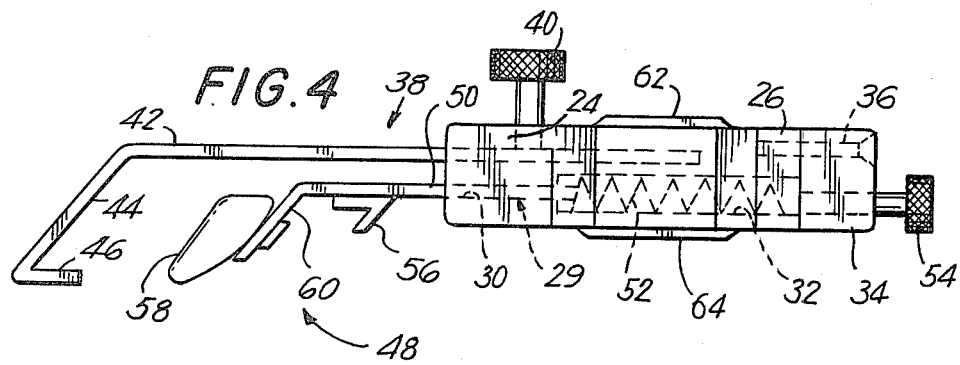
FIG. 4 is a side elevational view of the instrument shown in FIG. 3.

One embodiment of the instrument comprising the present invention is shown in FIGS. 3 and 4 and is designated generally by the reference character 20. The instrument 20 comprises a housing 22 having forward and rearward ends 24 and 26, respectively. A first, slot-like opening 28 is formed in the forward end 24 of the housing 22 and a second, two-part opening 29 comprising coaxial sections 30 and 32 is formed through the rearward end 26 of the housing 22. A closure member 34 is secured to the rearward end 26 of the housing 22 by means of fasteners 36 as shown in FIG. 2.

A primary arm, generally designated by the reference character 38, is slidably received within the first opening 28 and is adapted to be adjustably secured to the housing 22 by means of a set screw or other suitable fastener 40. The primary arm 38 is comprised of a first section 42 that is adjustably positioned in the slot 28, a second section 44 that is integral with and extends from the end of the first section 42 that is remote from the housing 22 and a third relatively short section 46 which, in the embodiment illustrated in FIG. 3 and in FIG. 4 is in a plane that is generally parallel to the plane of the first section 42. In a manner to be described more fully hereinafter, the third section 46 is adapted to releasably engage the transverse slot 12 formed in the bracket 10.

A secondary arm generally designated by the reference charcter 48 is also slidably and adjustably mounted in the housing 22. The secondary arm 48 comprises a first portion 50 that is adapted to be slidably received in the correspondingly sized and shaped section 30 of the opening 29. However, for purposes to be described more fully hereinafter, the section 30 is somewhat larger than the portion 50 of the secondary arm 48 in order to allow universal movement thereof. A helical compression spring 52 is positioned within the second section 32 in the housing and bears against the rearward end of the secondary arm 48 that extends through the section 30 of the opening 29 in the housing 22. The spring 52 exerts a forwardly directed force against the rearwardly facing end of the secondary arm 48 in order to urge the secondary arm 48 in the direction of the sections 44 and 46 of the primary arm 48. The spring force is controlled by a fastener 54 that is threaded through the closure member 34 and which bears against the rear end of the spring 52.

For purposes of convenience, a trigger 56 is provided on the underside of the secondary arm 48 in order to permit the orthodontist to retract or move the secondary arm 48 rearwardly in a direction away from the sections 44 and 46 of the primary arm 38. Finally, a universally movable labial plate 58 which will be described more fully hereinafter is also provided on the forward end 60 of the arm 48 that is remote from the housing 22.

As shown in FIGS. 3 and 4, bubble levels 62 and 64 are provided on the upper and lower surface of the housing 22 intermediate the ends 24 and 26 thereof. Adjacent each of the bubble levels 62 and 64 are indicia 66 which will indicate the extent of inclination of the primary arm 38 with respect to a horizontal plane when the orthodontist applies the bracket 10 to the tooth T.

Figure 5:
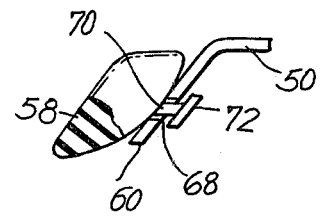
FIG. 5 is a fragmentary side elevational view, partially in section, illustrating a feature of the instrument shown in FIG. 3.

An important feature of the present invention is illustrated in FIG. 5. As mentioned hereinabove, it is desirable that the labial plate 58 be universally coupled to the secondary arm 48 so that, when in use, the plate 58 can accommodate itself to the many different inclinations and variations in tooth surfaces. One construction which permits universal play of the plate 58 relies on the slot section 30 being oversized with respect to the same dimensions of the portions 50 of the secondary arm 48. Another form of construction which is illustrated in FIG. 5, relies on the inherent resiliency of the plate 58 which may be made of a soft material such as rubber or the like. Alternatively, the rearward surface of the plate 58 may be provided with a stem 68 that extends through an oversized opening 70 formed in the end portion 60 of the secondary arm 48. In order to retain the plate 58, the stem 68 is provided with a head 72. It will be appreciated that any of the aforementioned forms of construction will provide some degree of universal movement to the plate 58. In this connection it should be noted that a great deal of movement is not required.

Figure 6A:
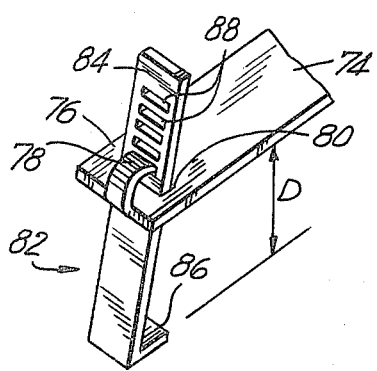
FIG. 6A is a fragmentary, perspective view of a modified portion of the instrument shown in FIG. 3 illustrating another feature of the present invention.

Turning now to FIG. 6 there is shown another important feature of the invention. Whereas in the first embodiment of the invention shown in FIG. 3 and FIG. 4 the primary arm 38 was of unitary construction, the alternative embodiment illustrated in FIG. 6A provides for some degree of adjustment of the portion of the primary arm that engages the transverse slot 12 in the bracket 10. In this alternative embodiment, the primary arm 74 is provided at its forward end 76 with a tab 78 and a slot 80. An L-shaped member 82, comprising legs 84 and 86 which are functionally equivalent to the sections 44 and 46, respectively, of the first embodiment of the primary arm 38 shown in FIGS. 3 and 4 is adjustably coupled to the forward end of the primary arm 74. That is, the leg 84 extends through the slot 80 and is releasably and adjustably secured thereto by means of the tab 78 which engages anyone of a plurality of slots 88 formed in the section 84. Thus it will be appreciated that the dimension D between the opposed surfaces of the sections 74 and 86 may be easily varied. This dimension D corresponds to the dimension between the slot 12 in the bracket 10 and the incisor ledge or cusp tip of the tooth T. As mentioned hereinabove, it is this dimension that is most critical in the accurate placement of the bracket 10.

Another alternative embodiment for selectively and securely placing the orthodontic bracket 10 on the lingual surface tooth T is shown in FIG. 7A. This embodiment comprises a plurality of primary arms 90 which define a set of arms 90a, 90b, 90c, etc. Each arm 90 has a different dimension H between sections 92 and 94 thereof. Since it is the section 92a that rests on the incisor ledge or cusp tip of the tooth T and the section 94a that engages the transverse slot 12 in each bracket 10, it will be appreciated that, by selectively placing the desired one of the arms 90 in the instrument 20, utilizing the set screw 40 to establish the axial relationship between the selected arm 90 and the housing 22 of the instrument 20, the bracket 10 may be placed at different heights on the vertical center line of the tooth T.

An alternative embodiment of the present invention is illustrated in FIG. 8. The first embodiment described hereinabove is particularly useful when the longitudinal axis of the instrument 20 can assume a position that is substantially perpendicular to the lingual mounting surface of the tooth. However, in those instances where this is not feasible, for example when there is limited space for the application of a bracket 10 on one of the molars, the embodiment illustrated in FIG. 8 can be utilized. This second embodiment contemplates the positioning of the longitudinal axis of the instrument in a plane that is substantially parallel to the lingual mounting surface of the tooth T.

The alternative instrument, generally designated by the reference character 100, comprises a housing 102 having a primary arm 104 is adjustably positioned thereon by means of a fastener 106 in much the same manner as described in connection with the first embodiment. The primary arm 104, at the end thereof that is remote from the housing 102, includes a transverse extension 107, that is adapted to contact the incisal edge or cusp tip of the tooth T that is to be treated. There is further provided a lip 108 that is adapted to releasably engage the transverse slot 12 in the bracket 10 in the same manner as described in connection with the first emboiment. If desired, a rib 110 as shown in FIG. 9A may be formed on the end of the primary arm 104 that is in opposition to the lip 108 for the purpose of supporting the bracket 10 on the underside thereof.

A secondary arm 112 is mounted intermediate the ends thereof on the housing 102, by means of a pivot pin 114 as shown in FIG. 8. The secondary arm 112 is comprised of first and second sections 116 and 118, respectively, the planes of which define an obtuse angle. The first section 116 of the secondary arm 112 is arranged to support a universally mounted labial plate 120 in much the same manner as described in connection with the first embodiment. The second section 118 of the secondary arm 112 is provided with a compression spring 122 which normally biases the plate 120 in a direction towards the facial surface of the tooth. By deflecting the second section 118 of the secondary arm 112 and thereby compressing the spring 122, the plate 120 will be displaced from the facial surface of the tooth T.

Also mounted on the housing 102 is a sleeve 124, on which is positioned a bubble level 126. It will be seen in FIG. 8 that the longitudinal axis of the bubble level 126 is substantially parallel to the longitudinal axis of the primary arm 104 and therefore substantially perpendicular to the longitudinal axis of the extension 107. Thus, by manipulating the instrument 100 about a generally horizontal axis that is substantially perpendicular to the longitudinal axis of the bubble level 126, the relationship of the slot 12 in the bracket 10 can be determined with respect to a predetermined plane, such as the horizontal plane for example. This relationship is of substantial importance because it is well known that the slot 12 in the bracket 10 should be parallel to the biting surface of the molars.

At this time it should be particularly noted, although it is not specifically illustrated, that each of the instruments 20 and 100, described hereinabove, could have two mutually perpendicular bubble levels on each of the surfaces thereof wherein only one has been described hereinbefore. While somewhat greater skill would be required in manipulating the instruments and reading the bubble levels, it will be appreciated that even more accurate placement of the bracket can be achieved since accurate determination of two mutually perpendicular planes can be read directly. Accordingly, it is intended that the scope of the present invention include two mutually perpendicular upper levels in two common, parallel planes.

Figure 6B:
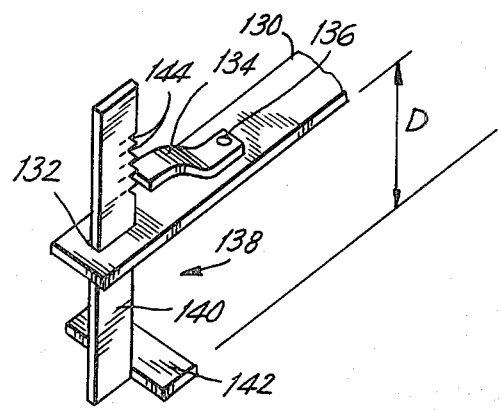
FIG. 6B is a fragmentary, perspective view of a portion of an alternative embodiment of the structure shown in FIG. 6A.

At this time, three modifications of structure hereinbefore discussed will be referred to in connection with FIGS. 6B, 7B and 9B. Referring first to FIG. 6B there is shown therein a modification of the structure illustrated in FIG. 6A. Whereas the leg 86 of the L-shaped member 82 in FIG. 6A is adapted to engage the horizontal slot 12 in the bracket 10, the structure shown in FIG. 6B is adapted to utilize the vertical slot 13 in the bracket 10. The outer end of a primary arm 130 is provided with an opening 132 therethrough as well as leaf spring 134 that is secured in place by means of fastener such as a rivet 136 or the like. An L-shaped member 138 is provided with a first leg 140 which is arranged to extend through the opening 132. The thickness of the leg 140 is approximately the same as or slightly less than the width of the slot 13 and is arranged to be received therein. At the lower end of the leg 140 there is another leg 142 which serves to support the lower edge of the bracket 10 when the leg 140 is positioned in the slot 13. It will be appreciated that by raising or lowering the L-shaped member 138 in the opening 132, the dimension D can be varied in much the same manner as that described in connection with the embodiment shown in FIG. 6A. That is, the bracket 10 may be placed at different heights from the incisal edge or cusp tip of the tooth T. To facilitate the displacement of the L-shaped member 138, it is desirable that the portion thereof extending above the primary arm 130 be provided with notches 144 which are adapted to be selectively engaged by the leaf spring 134. In this manner it will be a relatively simple matter to repeat critical dimensions. In addition, the portion of the L-shaped member 138 extending above the upper surface of the primary arm 130 also serves as means for visually aligning the bracket 10 parallel to the longitudinal axis of the tooth.

In FIG. 7B there is shown in a modification of the set of instruments shown in FIG. 7A. Whereas the set of instruments shown in FIG. 7A utilizes the horizontal slot 12 in the bracket 10 for determining the appropriate dimension H of the bracket 10 from the incisal edge or cusp tip of the tooth T, the set of instruments shown in FIG. 7B utilize the vertical slot 13 in the bracket 10 in order to permit a different dimension H to be selected. Each instrument 150a, 150b, 150c, etc. is comprised of a primary arm 152a, the outer end of which is provided with a downwardly depending leg 154a having a major plane that is perpendicular to the plane of the primary arm 152a. The edge 156a of the leg 154a is adapted to engage the vertical slot 13 in the bracket 10. A second leg 158a, which is in a plane parallel to and spaced from the plane of the primary arm 152a by a dimension $H_1$ is formed integrally at the lower end of the first leg 154a. From the foregoing it will be evident that by constructing a set of primary arms as hereinbefore described but with variations in the dimension H, a set of instruments will result that will permit the accurate placement of brackets 10 at different dimensions from the incisal edge or cusp tip of the tooth T.

The modification of the present invention shown in FIG. 9B represents the structure that may be used with a bracket 160 having a lingual tube 162 rather than the slots 12 and 13 as shown in the bracket 10. The bracket 160 is used primary on molars. The outer end of a primary arm 164 is provided with a transverse extension 166 in much the same manner as the embodiment shown in FIG. 8. A second arm 168 depends from the underside of the primary arm and is provided with an L-shaped pin 170 comprised of a first leg 172 and a second leg 174. When the transverse extension 166 rests on top of the tooth T the bracket 160 will be properly placed because the dimension between the transverse extension 166 and the second leg 174 of the L-shaped pin 170 is preset. Of course it is within the scope of the present invention, although not specifically illustrated, to provide means for varying the spacing between the second leg 174 of the pin 170 and the underside of the transverse extension 166 for the purpose of being able to place the bracket 160 at different vertical locations on the lingual surface of the tooth. It is also within the scope of the present invention to provide the instrument to which the primary arm 164 is attached with bubble level means as described hereinbefore so as to assure the parallel placement of the axis of the tube 162 with respect to the biting surface of the tooth T.

By utilizing one or more embodiments of the instrument comprising the present invention which is described hereinabove or by using any of the heretofore described modifications thereof, the method comprising the present invention may be practiced. To do so, a bracket is mounted on one portion of the instrument comprising the present invention utilizing either the vertical or the horizontal slot in the bracket. Another portion of the instrument comprising the present invention is then brought into engagement with the incisal edge or cusp tip of the tooth. The instrument is then manipulated while maintaining engagement of the second portion of the instrument with the incisal edge or cusp of the tooth until a desired dimension between the horizontal slot in the bracket and the incisal edge or cusp tip of the tooth is attained. The instrument may be manipulated until the bubble in the level means associated with the instrument assumes a predetermined position. This position indicates that the bracket is in the proper position with respect to the incisal edge or cusp tip of the tooth. Depending upon which embodiment of the invention is utilized, the instrument is manipulated about an axis that is either parallel to or perpendicular to the vertical axis of the tooth. Manipulation of one embodiment of the present invention about a horizontal axis will assure that either the horizontal slot or the lingual tube in the bracket is accurately located in a horizontal plane.

From the foregoing it will be evident than an improved method and instrument for positioning a lingual, orthodontic bracket has been disclosed. The instrument includes means for releasably engaging either the horizontal or vertical slot in the bracket or for engaging a lingual tube prior to adhesively securing the bracket to the lingual surface of the tooth. The various embodiments and modifications of the present invention are particularly applicable to positioning a lingual bracket directly on the tooth in a patient's mouth. Specifically, the bubble level means that are incorporated in the instrument comprising the present invention provides, in combination with suitable indicia on the instrument, effective means suitable for displaying the extent of inclination of a portion of the instrument with respect to a predetermined plane. In this manner the height of the bracket or the distance thereof from the incisal edge or cusp tip of the tooth may be very accurately determined. Thus, this accurate placement may be repeated from tooth to tooth as required.

There has been disclosed herebefore the best embodiments of the invention presently contemplated. However, it is to be understood that various changes and modifications may be made thereto without departing from the spirit of the invention.

What I claim as new and desire to secure by United States Letters Patent is:

1. An instrument for positioning a lingual orthodontic bracket, said instrument comprising:
   (a) a housing;
   (b) an arm extending from said housing and including means for releasably holding the orthodontic bracket at a position that is in opposition to the lingual surface of the tooth being treated; and
   (c) level indicating means for displaying the extent of inclination of said arm with respect to a predetermined plane.

2. The instrument according to claim 1, wherein said arm is adjustable in a direction that is substantially perpendicular to said predetermined plane.

3. The instrument according to claim 1 wherein said arm comprises a first leg adjustably coupled to said housing, a second leg coupled to and extending substantially perpendicularly from said first leg and a third leg coupled to said second leg, said third leg terminating in an edge portion that is adapted to releasably engage a slot in the bracket, said edge portion of said third leg and the confrontingly opposed surface of said first leg defining therebetween a dimension that determines the placement of the bracket with respect to the incisor ledge or cusp tip of the tooth.

4. The instrument according to claim 3 wherein said second leg is adjustably coupled to said first leg whereby the dimension between said edge portion of said third leg and the confrontingly opposed surface of said first leg is variable.

5. The instrument according to claim 4 wherein the end of said first arm that is remote from said housing includes a slot and a retaining tab and wherein said second leg extends through said slot and is releasably and adjustably engaged by said retaining tab.

6. The instrument according to claim 5 wherein the portion of said second leg that extends through said slot includes a plurality of spacedly calibrated notches each of which is adapted to be engaged by said retaining tab to thereby determine said dimension between said edge portion of said leg and the confrontingly opposed surface of said first leg.

7. The instrument according to claim 3, wherein there are a plurality of said arms thereby defining a set of arms having a range of said dimensions.

8. The instrument according to claim 1 wherein there is further included a labial plate and a second arm that is coupled to said housing in opposition to said means for releasably holding the bracket, said labial plate being mounted on said second arm and being adapted to engage the labial surface of the tooth when the bracket is positioned on the lingual surface of the tooth.

9. The instrument according to claim 8 wherein said labial plate is made of a resilient material.

10. The instrument according to claim 8 wherein said labial plate and said second arm are adjustably coupled to said housing.

11. The instrument according to claim 8 wherein said labial plate is universally coupled to said second arm.

12. The instrument according to claim 8 wherein said labial plate and said second arm are resiliently coupled to said housing.

13. The instrument according to claim 12 wherein spring means are included for resiliently biasing said labial plate towards the portion of said arm that releasably holds the orthodontic bracket.

14. The instrument according to claim 13 wherein there is further included means for varying the biasing force of said spring means.

15. The instrument according to claim 1 wherein said level indicating means is a bubble.

16. The instrument according to claim 15 wherein said level indicating means is mounted in said housing.

17. The instrument according to claim 16 wherein there are two of said level indicating means on two opposed surfaces of said housing which are in opposition to each other.

18. The instrument according to claim 17 wherein said housing includes indicia adjacent each said level indicating means.

19. The instrument according to claim 1 wherein said arm is adjustable in a plane that is substantially parallel to said predetermined plane.

20. The instrument according to claim 1 wherein the bracket has a slot and wherein said means for releasingly holding the bracket comprises an elongated member adapted to to be received in the slot.

21. The instrument according to claim 20 wherein the slot in the bracket and the elongated member that is adapted to be received therein are both in substantially horizontal planes when the bracket is positioned on a tooth.

22. The instrument according to claim 21 wherein said elongated member is vertically adjustable.

23. The instrument according to claim 20 wherein the slot in the bracket and the elongated member that is adapted to be received therein are both in substantially vertical planes when the bracket is positioned on a tooth.

24. The instrument according to claim 23 wherein said elongated member is vertically adjustable.

25. A method for positioning a bracket on the lingual surface of a tooth by means of an instrument having level indicating means thereon, said method comprising the steps of:
(a) releasably holding the bracket on a first portion of an instrument at a fixed location with respect to a second portion of the instrument; ;p1 (b) engaging the incisal edge or cusp tip of the tooth with the second portion of the instrument;
(c) manipulating the instrument while maintaining engagement of the second portion thereof with the incisal edge or cusp tip of the tooth until the level indicating means reaches a predetermined position that corresponds to the desired location of the bracket; and
(d) securing the bracket to the lingual surface of the tooth at the desired location.

26. The method according to claim 25 wherein said manipulating step comprises rotating the first portion of the instrument about an axis that is substantially parallel to the vertical axis of the tooth.

27. The method according to claim 25 wherein said manipulating step comprises rotating the first portion of the instrument about an axis that is substantially perpendicular to the vertical axis of the tooth.

28. The method according to claim 25 wherein the step of releasably holding the bracket comprises engaging the first portion of the instrument in a horizontal slot in the bracket.

29. The method according to claim 25 wherein the step of releasably holding the bracket comprises engaging the first portion of the instrument in a vertical slot in the bracket.

30. The method according to claim 25 wherein the step of releasably holding the bracket comprises engaging a lingual tube on the bracket by means of a pin on the first portion of the instrument.

* * * * *